United States Patent [19]

Cuca et al.

[11] Patent Number: 5,554,379
[45] Date of Patent: Sep. 10, 1996

[54] LONG ACTING GI AND ESOPHAGEAL PROTECTANT

[75] Inventors: Robert Cuca, Edwardsville, Ill.; Keith Lienhop, St. Charles, Mo.; Thomas Riley, Manchester, Mo.; Mitchell I. Kirschner, University City, Mo.; R. Saul Levinson, Chesterfield, Mo.

[73] Assignee: KV Pharmaceutical Company, St. Louis, Mo.

[21] Appl. No.: 262,254

[22] Filed: Jun. 20, 1994

[51] Int. Cl.⁶ .................................. A61K 47/00
[52] U.S. Cl. ........................................... 424/439
[58] Field of Search ............................... 424/439

[56] References Cited

U.S. PATENT DOCUMENTS

| | | |
|---|---|---|
| 4,011,661 | 3/1977 | Sezaki et al. . |
| 4,040,857 | 8/1977 | Lissant . |
| 4,184,978 | 1/1980 | France et al. . |
| 4,280,996 | 7/1981 | Okamoto et al. . |
| 4,340,594 | 7/1982 | Mizushima et al. . |
| 4,385,049 | 5/1983 | Cuca . |
| 4,439,194 | 3/1984 | Harwood et al. . |
| 4,542,020 | 9/1985 | Jackson et al. . |
| 4,551,148 | 11/1985 | Riley, Jr. et al. . |
| 4,606,913 | 8/1986 | Aronson et al. . |
| 4,698,359 | 10/1987 | Niederer et al. . |
| 4,720,353 | 1/1988 | Bell . |
| 4,831,018 | 5/1989 | Kirsh et al. . |
| 4,857,335 | 8/1989 | Bohm . |
| 4,874,605 | 10/1989 | Urban, Jr. et al. . |
| 4,891,208 | 1/1990 | Janoff et al. . |
| 4,960,764 | 10/1990 | Fignerao, Jr. et al. . |
| 5,010,067 | 4/1991 | Handley et al. . |
| 5,019,397 | 5/1991 | Wong et al. . |
| 5,055,303 | 10/1991 | Riley, Jr. . |
| 5,215,758 | 6/1993 | Krishnamurthy . |

OTHER PUBLICATIONS

CA119:125078 (1993).

*Primary Examiner*—Paul J. Killos
*Attorney, Agent, or Firm*—Gary M. Nath; Nath & Associates

[57] ABSTRACT

A bioadherent, orally ingestible system, which comprises: a water-in-oil system having at least two phases, one phase comprises from about 75% to about 99% by volume of an internal hydrophylic phase and the other phase comprises from about 25% to about 1% by volume of an external hydrophobic phase, wherein the external hydrophobic phase comprises two components, one component being about 3% to about 97% by volume of the hydrophobic phase of a hydrophobic oil and the other being about 97% to about 3% of an emulsifier having a HLB value less than about 10.

15 Claims, No Drawings

LONG ACTING GI AND ESOPHAGEAL PROTECTANT

BACKGROUND OF THE INVENTION

1. Field of the Invention

This invention relates to stable water-in-oil emulsions that are usable as bioadherent, ingestible systems. The systems are designed to coat and adhere to epithelial and mucosal membranes of the esophagus and gastrointestinal (GI) tract for extended periods of time. The purpose of the coating is to protect the membranes of the esophagus and GI tract against gastric fluid, while promoting healing caused by esophagitis, ulcers, and so forth and to release active drug over a controlled release rate.

2. Description of the Prior Art

Although a need for water-in-oil emulsions having a high water or aqueous phase content has long existed for use in pharmaceuticals, cosmetic and toiletry preparations, such as night creams or barrier creams, moisturizing creams and lotions, it has been difficult to provide such emulsion where the aqueous phase exceeds 45% to 55% on a weight to weight basis. Although many benefits are to be derived from providing a high water content in a water-in-oil emulsion system for cosmetic applications in particular, formulators have not heretofore been able to add more than about 50% water to the emulsion without seriously affecting the shelf life stability of the preparation. It is to be appreciated in this respect that because of the time delay that occurs between formulation of a product and commercial sale, it is undesirable to employ an emulsion which will break in a short period of time, particularly when exposed to temperature extremes that are encountered during transportation and warehouse storage. Although stability under normal climatic conditions is an asset, at the very minimum the emulsion system should be able to withstand temperatures on the order of 43° C. (110° F.) for at least six months without breaking.

Water-in-oil emulsions are used in barrier preparations or pore-occluding products to provide a thin oleaginous layer over the areas of the user's skin to which the composition is applied. Increasing the amount of hydrophilic inner phase in the emulsion decreases the oily feel of the material without deleteriously effecting the overall utility of the formulation. Such formulations have greater customer appeal because the higher hydrophilic content enhances the evaporative and thereby cooling effect of the cream or lotion upon application. Products formulated from these emulsion systems are described in U.S. Pat. No. 4,385,049 to Robert C. Cuca.

The use of water-in-oil emulsions as a liquid or semi-liquid system for oral use have not been successful. U.S. Pat. No. 2,948,686 to Gianladis describes water-in-oil emulsions but the patentee was not able to incorporate more than about 52% water in his emulsion system.

The present invention overcomes these deficiencies by preparing an orally useable and stable emulsion or suspension having at least 75% of an internal hydrophylic phase with a multifunctional hydrophobic external phase containing an oil and mixtures of emulsifiers in high concentrations. Such systems enable the inventive formulation, when taken orally to coat and protect the membranes of the esophagus and GI tract against high acidity and reflux conditions while enabling an optional active drug to be released from the formulation over controlled rates of release.

SUMMARY OF THE INVENTION

This invention relates to the preparation of a bioadherent, orally ingestible system, which comprise: a water-in-oil system having at least two phases, one phase comprises from about 75 to about 99% by volume of an internal hydrophylic phase and the other phase comprises from about 25% to about 1% by volume of an external hydrophobic phase, wherein the external hydrophobic phase is composed of two components, one component being about 3 to about 97% of a hydrophobic oil and the other being about 97% to about 3% of an emulsifier having a HLB value less than 10.

In a preferred embodiment the hydrophylic phase contains an active pharmaceutical material which may be selected from the group consisting of water-soluble antacids, analgesics, anti-inflammatories, antihistamines, antitussives, expectorants, decongestants, narcotics, antibiotics, bronchodilators, minerals and mixtures thereof or other drugs used to treat the esophagus or gastrointestinal tract.

In another preferred embodiment the water-insoluble active pharmaceutical material in the hydrophobic phase may be selected from the group consisting of water-insoluble antacids, analgesics, anti-inflammatories, antihistamines, antitussives, expectorants, decongestants, narcotics, antibiotics, bronchodilators, minerals and mixtures thereof or other drugs used to treat the esophagus or gastrointestinal tract.

Additional preferred embodiments involve selecting the hydrophylic phase from water, glycerine, sorbital solutions, sugar syrups, polymer solutions and mixtures thereof. In contrast, the hydrophobic oil is selected from the group consisting of mineral oil, natural or synthetic vegetable oil, long chain fatty acids and alcohols of straight chain alkyls having from 12 to 32 carbon atoms, waxes and mixtures thereof, whereas the emulsifier present in the hydrophobic phase is selected from the group consisting of sorbitan esters, polyglycerol esters of fatty acids, glycerol esters of fatty acids, 1 to 5 mole ethoxylates of fatty acids or esters, saccharides derivatives and mixtures thereof.

In a further embodiment of the invention, a method is provided for treating an esophageal or GI tract disorder, which comprises administering to the oral cavity a therapeutically effective amount of a bioadherent, orally ingestible system, which comprises: a water-in-oil system having at least two phases, one phase comprises from about 75% to about 99% by volume of an internal hydrophylic phase the other phase comprises from about 25% to about 1% by volume of an external hydrophobic phase, and wherein the external hydrophobic phase is comprised of two components, one component being about 3% to about 97% by volume of the hydrophobic phase of a hydrophobic oil and the other being about 97% to about 3% of an emulsifier having a HLB value less than about 10.

DETAILED DESCRIPTION OF THE INVENTION

The present invention provides an emulsion or suspension having varying viscosities and flow characteristics. Preferably the system is a liquid or semi-solid emulsion or suspension system or a solid emulsion that liquifies at body temperatures to be taken orally for the purpose of coating esophageal and GI tract membranes. This system is intended to remain in place for extended periods of time and can serve as a reservoir for the delivery of drug or pH modifying ingredients. The property common to all formulations of the invention is the coating and adhering of the system to mucosal membranes of the esophagus and GI tract for extended periods of time. The formulations coat and protect membranes of the esophagus and GI tract against gastric fluid, while promoting healing of esophagitis and ulcers. The resulting protective layer also has the potential to provide a reservoir of drugs or pH modifying ingredients. The formulations may contain an extended release buffer for controlling pH over an extended period of time by prolonged stomach residence through adhesion to esophagus and villi as well as through swelling and resisting pylorus dumping. In addition, the film layer, which is amorphous in structure when adherred to biological tissue, continually adjusts itself with organ muscalature creating a symbiotic, therapeutic device residing for extended periods of time in the target issue, such as in the stomach. Because of the unique emulsion system, the protective film has the potential to increase in thickness as time goes on by absorption of resident fluids into the hydrophylic layer of the system. This can then provide a thicker layer as a protectant. Prior are polymer systems have the potential to wash away quickly.

The phrase esophageal or GI tract disorders relates to those disorders found in the esophagus, functional dyspepsia and from other nonspecific gastrointestinal complaints, gastrointestinal bleeding, disorders of the esophagus, stomach, and duodenum, acute abdomen and surgical gastroenterology, diarrhea and constipation, gastroenteritis, inflammatory diseases of the bowel and so forth. Specific disorders include the following:

Pre-esophageal dysphagia; esophageal dysphagia; gastroesophageal reflux; corrosive esophagitis and stricture such as a) esophageal diverticula b) hiatus hernia (or gastroesophegial reflux disease (GERD))

c) esophageal laceration and rupture, and d) infectious disorders of the esophagus; functional dyspepsia; nausea and vomiting; globus sensation; adult remination; halitosis, real and imagined; arteriovenous malformations; gastritis; peptic ulcer; neoplasms of the stomach; abdominal pain; peritonitis; pancreatitis; cancer of the pancreas; diarrhea; constipation; gastroenteritis due to bacterial enterotoxins; hemorrhagic colitis; staphylococcal food poisoning; botulism; malabsorption syndromes such as
 i) carbohydrate intolerance
 ii) celiac disease
 iii) tropical spruce
 iv) whipple's disease
 v) intestinal lymphangiectasia and
 vi) infection and infestation; crohn's disease; ulcerative colitis and so forth.

The present system is composed of two phases; a hydrophylic inner phase and a hydrophobic external phase. More particularly, the present system comprises a water-in-oil system having at least two phases, one phase comprises from about 75 to about 99% by volume of an internal hydrophylic phase and the other phase comprises from about 25% to about 1% by volume of an external hydrophobic phase. A unique feature of external hydrophobic phase is that it is comprised of two components, one component being about 3 to about 97% by volume of the hydrophobic phase of a hydrophobic oil and the other being about 97% to about 3% by volume of the hydrophobic phase of an emulsifier having a HLB value less than about 10.

The hydrophilic polymer phase is present in the delivery system in amounts of about 75% to about 99% and preferably about 80% to about 90% by volume of the overall system. As discussed above, the hydrophilic polymer phase is present in amounts far greater than the external hydrophobic phase and is situated to enable the retention of active material, when used.

Preferably the hydrophylic phase is selected from the group consisting of water, glycerine, sorbitol solutions, sugar syrups, polymer solutions and mixtures thereof. The hydrophilic polymer material does not have to have any solubility in the hydrophobic phase and is preferably selected from water and sorbitol solutions, such as solutions containing 70% by volume sorbitol. A variety of natural polymers or derivatives thereof as well as synthetic polymers may also be used. Exemplary polymers include polyethylene glycol polymers having mean average molecular weight of at least 1000 and preferably from about 2000 to 2 million or more. Exemplary sugar syrups include corn syrup, high fructose corn syrup and exemplary sugar solutions include cane sugar solutions, dextrose solutions, lycasin and so forth.

The hydrophobic phase is present in the delivery system in amounts far less than the internal phase. In general amounts of about 25% to about 1% by volume of the system are useable with preferred amounts of about 20% to about 10% being used. The hydrophobic phase is specifically designed to avoid the prior use of low amounts of emulsifier. In particular the present system is composed of two components, a hydrophobic oil and an emulsifier.

Generally amounts of hydrophobic oil of about 3% to about 97% are used in the external system, based on the weight of the external system. In addition, amounts of about 3% to about 97% of the emulsifier are also present in the external phase. By raising the emulsifier content in the external phase to be about or less than 50% of the oil phase, an adhesive formulation is prepared which will adhere to the GI tract mucoso lining. The configuration of the external phase is critical to prevent the internal phase from coalescing and disintegrating after use. By using relatively high levels of emulsifiers and blends thereof, the capability of the internal phase to absorb aqueous components is enhanced.

The hydrophobic oil may be selected from a wide variety of materials, and is preferably a mineral oil, natural or synthetic vegetable oil, long chain fatty acids and alcohols of straight chain alkyls having from 12 to 32 carbon atoms, waxes and mixtures thereof.

Any physiologically acceptable orally useable oil or mixtures thereof including those oils which satisfy the specifications of the United States Pharmacopeia or National Formulary may be utilized in the practice of the invention. Representative members include peanut oil, safflower oil, soya bean oil, cottonseed oil, light mineral oil, corn oil, olive oil, sesame oil, almond oil, castor oil, isopropyl myristate and coconut oil. Of particular preference is mineral oil.

Particularly preferred wax materials are selected from animal waxes, vegetable waxes, petroleum waxes, synthetic waxes, and mixtures thereof and include without limitation beeswax, lanolin, candelilla wax, carnauba wax, microcrystalline wax, carbowax, and mixtures thereof. Furthermore, the wax material may be selected from the group consisting of lauric acid, myristic acid, palmitic acid, stearic acid, oleic acid, linoleic acid, linolenic acid, and mixtures thereof.

The emulsifier used in the formulations of this invention find utility for preventing the internal phase from coalescing and disintegrating after used. It has the advantage of increasing the efficacy of any drug used over that obtainable with commercial formulations. Another desirable feature is that it is free of extraneous ionic materials that may be present in prior art preparations. Preferred emulsifiers have a HLB value less than about 10 in order to obtain these desirable features. HBL is a qualitative description for emulsifiers wherein the ratio of hydrophile to lipophile can be assessed. Emulsifiers with HLB's below 10 are more lipid soluble than water soluble and tend to form stable water-in-oil emulsions.

The emulsifier is preferably selected from sorbitan esters, polyglycerol esters of fatty acids, glycerol esters of fatty acids, 1 to 5 mole ethoxylates of fatty acids or esters, saccharide derivatives and mixtures thereof. Particularly preferred emulsifiers are selected from the group consisting of polyglycerol oleate, sorbitan monooleate, glycerol monooleate and mixtures thereof.

Examples of saccharide derivatives include fatty acid saccharide derivatives such as sucrose oleate and sucrose stearate. Examples of glycerol and polyglycerol esters include mono, di, tri and polyglycerol esters with oleaic acid and stearic acid. The carbon chain length of the fatty acids may be from about $C_{10-22}$ and preferably is from about $C_{12-18}$.

The formulations viscosities are prepared to have a liquid to semi-liquid consistency, that is they may range from being pourable to having a semi-thick consistency. Solid emulsion formulations that liquify at body temperature are also achievable and are desirable where portability and ease of use by a patient are important. When using solid or semi-solid viscosities it is important that after the formulation is taken orally for it to start to exhibit a flow character to enable coating of the GI tract. Thicker materials do not coat well and remain as a bolus in the stomach. Thinner viscosities tend to flow too easily and do not coat uniformly and may pass through the GI tract too quickly. Preferably viscosity ranges of about 20,000 to over 1 million centipoise are effective herein. If the viscosities are too low, the emulsion destabilizes and comes apart, rendering the product unuseable.

The formulations of the invention may be used as is when preblended with an active material or drug when being prepared. While not being limited thereto, water-soluble drugs are preferably used in the hydrophylic internal phase whereas water-insoluble drugs are present in the external hydrophobic phase.

The active material(s) or drug(s) may be described as a single drug entity or a combination of entities. The delivery system is designed to be used with drugs having high water-solubility as well as with drugs having low water-solubility to produce a drug delivery system that has controlled release rates. The term "drug" includes without limitations, medicaments, vitamins, mineral supplements and other chemical or biological substances intended for use in the treatment, prevention, diagnosis, cure or mitigation of disease or illness of the gastrointestinal tract or substances which affect the structure or function of the gastrointestinal tract body; all herein referred to as a "disorder."

Suitable categories of drugs that may be employed in the instant application may vary widely and generally represents any stable drug or combination thereof. Illustrative categories and specific examples include: (a) antitussives, such as dextromethorphan, dextromethorphan hydrobromide, noscapine, carbetapentane citrate, and chlophedianol hydrochloride; (b) antihistamines, such as chlorpheniramine maleate, phenindamine tartrate, pyrilamine maleate, doxylamine succinate, and phenyltoloxamine citrate; (c) decongestants, such as phenylephrine hydrochloride, phenylpropanolamine hydrochloride, pseudoephedrine hydrochloride, ephedrine; (d) various alkaloids, such as codeine phosphate, codeine sulfate and morphine; (e) mineral supplements such as potassium chloride, zinc chloride and calcium carbonates, magnesium oxide and other alkali metal and alkaline earth metal salts; (f) laxatives, vitamins and antacids (g) ion exchange resins such as cholestryramine; (h) anti-cholesterolemic and anti-lipid agents; (i) antiarrhythmics such as N-acetyiprocainamide; (j) antipyretics and analgesics such as acetaminophen, aspirin and ibuprofen; (k) appetite suppressants such as phenylpropanolamine hydrochloride or caffeine; and (l) expectorants such as guaifenesin; and (m) antacids such as aluminum hydroxide and magnesium hydroxide.

Additional useful active medicaments include anti-inflammatory substances, coronary dilators, cerebral dilators, peripheral vasodilators, anti-infectives, psychotropics, antimanics, stimulants, laxatives, gastrointestinal sedatives, antidiarrheal preparations, antianginal drugs, anticoagulants and antithrombotic drugs, hypnotics, sedatives, anti-emetics, anti-nauseants, anticonvulsants, neuromuscular drugs, hyper- and hypo-glycemic agents, thyroid and antithyroid preparations, diuretics, antispasmodics, uterine relaxants, antiobesity drugs, anabolic drugs, erythropoietic drugs, antiasthamatics, cough suppressants (anti-tussives), mucolytics, anti-uricemic drugs, and the like.

The drugs are used in amounts that are therapeutically effective. While the effective amount of a drug will depend on the drug used, amounts of drug from about 5% to about 65% have been easily incorporated into the present delivery systems while achieving controlled release.

The systems may be prepared by continuous or batch processes. As in preparing conventional emulsions, shear force is applied to the system components by use of homogenizers, mills, impingement surfaces, ultra-sound, shaking or vibration. Unlike conventional emulsions, the mixing shear should be at low levels in order to prevent destruction of the system by imparting excess energy. Temperature is not usually a critical factor in the preparation of the systems. The temperatures utilized will be dependent upon the final end product desired.

The systems may be prepared by mixing the internal with the external phase in a planetary-type mixer. Another manner of preparing the system is by use of a continuous mixer which comprises multiple impellers. The external phase is first introduced into the continuous mixer until it reaches the level of the lowest impeller in the mixing chamber. The two phases are then simultaneously introduced through the bottom of the mixer in proper proportion as its impeller or impellers rotate to apply a shear to the components. The finished product emerges through the top of the mixer. The actual speed of the impeller or impellers will vary, depending upon the product produced as will the rate of flow of the two phase streams.

In a preferred embodiment, the active agent or drug and ingredients of the internal phase were mixed together at room temperature (24° C.). The ingredients of the external phase were mixed together in a separate vessel. The internal phase composition was slowly added to the external phase composition as the two phases are mixed together at low shear until the desired viscosity was obtained.

It is believed that the release mechanism of active components may be a combination of several phenomena once the formulation is adhered to the GI tract. Enzymatic degradation of the system, diffusion of the drug through the system, competitive adsorption, desorption of hydrophobic components from hydrophilic surface centers, convection of the drug through mesopores and macropores, diffusion of the external medium into the system by way of solubility or capillary action through porous structures created by the addition of hydrophilic polymers or water-soluble solids, as well as expansion of drug and/or system from water absorption into the inner phase.

The delivery system may also be used in combination with one or more conventional excipients. The term "excipients" as used herein mean substances and materials generally used in the drug or food industry which do not alter the character and function of the active component or oral system.

Flavors which may optionally be added to the delivery system are those well known in the pharmaceutical art. For example, synthetic flavor oils, and/or oils from plants, leaves, flowers, fruits and so forth, and combinations thereof are useful.

Representative flavor oils include spearmint oil, peppermint oil, cinnamon oil, and oil of wintergreen (methylsalicylate). Also useful are artificial, natural or synthetic fruit flavors such as citrus oils including lemon, orange, grape, line and grapefruit, and fruit essences including apple, strawberry, cherry, pineapple, and so forth.

The amount of flavoring agent employed is normally a matter of preference subject to such factors as flavor type, base type and strength desired. In general, amounts of about 0.05% to about 25.0% by weight of the final product are useful with amounts of about 0.3% to about 1.0% being preferred and about 0.8% to about 8% being most preferred.

The delivery system may contain a sweetening agent. Sweetening agents may be selected from a wide range of materials such as water-soluble sweetening agents, water-soluble soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup sol ids and sugar alcohol s such as sorbitol, xylitol, mannitol and mixtures thereof.

B. Water-soluble artificial sweeteners such as the soluble saccharin salts, i.e., sodium or calcium saccharin salts, cyclamate salts, acesulfam-K and the like, and the free acid form of saccharin.

C. Dipeptide based sweeteners such as L-aspartyl L-phenylalanine methyl ester and materials described in U.S. Pat. No. 3,492,131 and the like.

While delivery systems based on the instant invention are generally liquid, semi-solid or solid, it is contemplated that they may be employed, with or without the conventional supplemental agents, as principal components of systems to be dissolved or dispersed in water or other ingestible liquids for ingestion in a drinkable form.

The excipients are added to the oral delivery system anytime during processing. It should be recognized that certain excipients should be added prior to, during or after the active material is blended into the system in order to achieve uniform distribution of the ingredients. Preferably, excipients in liquid form are added before the active material whereas powdered excipients may be added before or after the active material is added.

The following examples are illustrative of preferred embodiments of the invention and are not to be construed as limiting the invention thereto. All percentages are based on the percent by weight of the delivery system unless otherwise indicated and all totals equal 100% by weight.

EXAMPLE 1

This example describes the preparation of a long acting GI tract and esophogeal protectant.

In separate vessels the internal phase and external phases were prepared with the components identified below. Once prepared the internal phase was added incrementally to the external phase while blending the mixture.

The internal phase may be prepared by placing the water into containers and heating to 70°–80° C. The sorbitol is then added and the system mixed to form a homogenous mixture. The parabens are then added and mixed until they are dissolved (about 15 minutes). The system is then cooled to about 35° C. or less.

The external phase is prepared by blending the oil and polyglycerol together, such as in a blender, for about 15 minutes.

The emulsion is then formed by adding the internal phase to the external phase while mixing. Mixing is continued for several minutes to form a stable emulsion.

|  | Wt % |
|---|---|
| Internal Phase |  |
| Water | 72.8 |
| Sorbitol 70% | 8.0 |
| Methylparaben | 0.13 |
| Propylparaben | 0.07 |
| External Phase |  |
| Mineral Oil | 10.0 |
| Polyglycerol Oleate | 9.0 |

EXAMPLE 2

This example describes the preparation of a long acting GI tract and esophogeal protectant with an antacid compound added to the internal phase.

In separate vessels the internal phase and external phases were prepared with the components identified below according to the procedure set forth in Example 1.

The internal phase was prepared by putting the glycerin into a vessel and warming it to 70°–80° C. The methyl and propyl parabens are then added and stirred until they dissolve (about 10 minutes). While stirring add the potassium sodium tartrate with Mg (OH)$_2$ and Al (OH)$_3$ to the mixture at about 40° C. Add sucrose and stir until it dissolves, about 10 minutes.

|  | Wt % |
|---|---|
| Internal Phase |  |
| Glycerin | 22.99 |
| Methylparaben | 0.1 |
| Propylparben | 0.01 |
| Potassium sodium tartrate | 0.9 |
| Mg(OH) 3.7% potassium | 14.0 |
| Al(OH)$_3$ gel | 28 |
| Sucrose | 15.0 |
| External Phase |  |
| Mineral Oil | 10.0 |
| Polyglycerol Oleate | 9.0 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A long acting, bioadherent, orally ingestible delivery system which consists essentially of: a water-in-oil system having at least two phases, one phase comprises from about 75% to about 99% by volume of an internal hydrophilic polymer phase selected from the group consisting of water, glycerin, sorbitol solutions, sugar syrups, polymer solutions and mixtures thereof, and the other phase comprises from about 25% to about 1% by volume of an external hydrophobic phase, wherein the external hydrophobic phase is comprised of two components, one component being about 3% to about 97% by weight of said hydrophobic phase of a hydrophobic oil selected from the group consisting of mineral oil, natural or synthetic vegetable oil, long chain fatty acids and alcohols of straight chain alkyls having from 12 to 32 carbon atoms, waxes and mixtures thereof, the other being about 97% to about 3% by weight of said hydrophobic phase of an emulsifier having a HLB value less than 10 selected from the group consisting of sorbitan esters, polyglycerol esters of fatty acids, glycerol esters of fatty acids, 1 to 5 mole ethoxylates of fatty acids or esters, saccharides, derivatives and mixtures thereof.

2. The ingestible system of claim 1, wherein the hydrophylic phase contains an active pharmaceutical material.

3. The ingestible system of claim 2, wherein the active pharmaceutical material is selected from the group consisting of water-soluble antacids, analgesics, anti-inflammatories, antihistamines, antitussives, expectorants, decongestants, narcotics, antibiotics, bronchodilators, minerals and mixtures thereof.

4. The ingestible system of claim 1, wherein the phase is in the form of an emulsion or suspension.

5. The ingestible system of claim 1, wherein the internal phase is present in amounts of about 80 to about 90% by volume.

6. The ingestible system of claim 1, wherein the external phase contains an active pharmaceutical material.

7. The ingestible system of claim 6, wherein the active pharmaceutical material is selected from the group consisting of water-insoluble, antacids, analgesics, anti-inflammatories, antihistamines, antitussives, expectorants, decongestants, narcotics, antibiotics, bronchodilators, minerals and mixtures thereof.

8. The ingestible system of claim 7, wherein the emulsifier is selected from the group consisting of polyglycerol oleate, sorbitan monooleate, glycerol monooleate and mixtures thereof.

9. The ingestible system of claim 1, wherein the external phase is present in amounts of about 20% to about 10% by volume of the entire system.

10. The ingestible system of claim 1, wherein the wax is selected from the group consisting of animal waxes, vegetable waxes, synthetic waxes and mixtures thereof.

11. A method for treating an esophageal or GI tract disorder, which consists essentially of: administering orally a therapeutically effective amount of a long acting, bioadherent, orally ingestible delivery system, which comprises: a water-in-oil system having at least two phases, one phase comprises from about 75% to about 99% by volume of an internal polymer hydrophilic phase selected from the group consisting of water, glycerin, sorbitol solutions, sugar syrups, polymer solutions and mixtures thereof, and the other phase comprises from about 25% to about 1% by volume of an external hydrophobic phase, wherein the external hydrophobic phase is comprised of two components, one component being about 3% to about 97% by weight of said hydrophobic phase of a hydrophobic oil selected from the group consisting of mineral oil, natural or synthetic vegetable oil, long chain fatty acids and alcohols of straight chain alkyls having from 12 to 32 carbon atoms, waxes and mixtures thereof, and the other being about 97% to about 3% by weight of said hydrophobic phase of an emulsifier having a HLB value less than 10 selected from the group consisting of sorbitan esters, polyglycerol esters of fatty acids, glycerol esters of fatty acids, 1 to 5 mole ethoxylates of fatty acids or esters, saccharides, derivatives and mixtures thereof.

12. The method of claim 11, wherein the hydrophylic phase contains an active pharmaceutical material selected from the group consisting of water-soluble antacids, analgesics, anti-inflammatories, antihistamines, antitussives, antibacterials, expectorants, decongestants, narcotics, antibiotics, bronchodilators, minerals and mixtures thereof.

13. The method of claim 11, wherein the hydrophobic phase contains an active pharmaceutical material selected from the group consisting of water-insoluble, antacids, analgesics, anti-inflammatories, antihistamines, antitussives, expectorants, decongestants, narcotics, antibiotics, bronchodilators, minerals and mixtures thereof.

14. The method of claim 11, wherein the internal phase is present in amounts of about 80 to about 90% by volume.

15. The method of claim 11, wherein the emulsifier is selected from the group consisting of polyglycerol oleate, sorbitan monooleate, glycerol monooleate and mixtures thereof.

* * * * *

UNITED STATES PATENT AND TRADEMARK OFFICE
CERTIFICATE OF CORRECTION

PATENT NO. : 5,554,379  
DATED : Sep. 10, 1996  
INVENTOR(S) : Robert CUCA et al It is certified that error appears in the above-indentified patent and that said Letters Patent is hereby corrected as shown below:

Column 3, line 16, change "are" to -- art --.

Column 3, line 48, change "crohn's" to -- Crohn's --.

Column 4, line 61, change "used" to -- use --.

Column 5, line 2, change "10" to -- 10 --.

Column 7, line 16, change "line" to -- lime --.

UNITED STATES PATENT AND TRADEMARK OFFICE
CERTIFICATE OF CORRECTION

PATENT NO. : 5,554,379
DATED : Sept. 10, 1996
INVENTOR(S) : Robert Cuca et al

It is certified that error appears in the above-indentified patent and that said Letters Patent is hereby corrected as shown below:

Column 7, line 27, change "soluble soluble" to -- soluble --.

Claim 5, column 9, line 34, change "80" to -- 80% --.

Claim 8, column 9, line 44, change "claim 7" to -- claim 1 --.

Claim 14, column 10, line 42, change "80" to -- 80% --.

Signed and Sealed this

Tenth Day of December, 1996

*Attest:*

BRUCE LEHMAN

*Attesting Officer*     *Commissioner of Patents and Trademarks*